United States Patent
Dockery et al.

(10) Patent No.: US 7,153,896 B2
(45) Date of Patent: Dec. 26, 2006

(54) ELEMENT FOR PROTEIN MICROARRAYS

(75) Inventors: Kevin P. Dockery, Rochester, NY (US); David M. Teegarden, Pittsford, NY (US); Tiecheng A. Qiao, Webster, NY (US); Brian J. Antalek, Livonia, NY (US); Susan Power, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 257 days.

(21) Appl. No.: 10/714,205

(22) Filed: Nov. 14, 2003

(65) Prior Publication Data
US 2005/0107528 A1 May 19, 2005

(51) Int. Cl.
C08K 5/3435 (2006.01)

(52) U.S. Cl. .................. 524/100; 524/22; 525/54.1; 427/2.13; 428/478.2

(58) Field of Classification Search .......... 524/22, 524/100; 525/54.1; 427/2.13; 428/478.2
See application file for complete search history.

(56) References Cited

U.S. PATENT DOCUMENTS

| 4,988,814 | A | * | 1/1991 | Abou-Gharbia et al. | .... 544/295 |
| 6,642,383 | B1 | * | 11/2003 | Lazzari et al. | .............. 544/383 |
| 6,815,078 | B1 | * | 11/2004 | Qiao et al. | ............... 428/478.2 |
| 2003/0170474 | A1 | | 9/2003 | Qiao et al. | |

FOREIGN PATENT DOCUMENTS

| EP | 1106603 A2 | 6/2001 |
| WO | 95/04594 | 2/1995 |
| WO | 00/04382 A1 | 1/2000 |
| WO | 00/04389 | 1/2000 |
| WO | 01/40312 A2 | 6/2001 |
| WO | 01/40803 A1 | 6/2001 |

OTHER PUBLICATIONS

Pavel Arenkov, et al., "Protein Microchips: Use for Immunoassay and Enzymatic Reactions". Jun. 7, 1999, Analytical Biochemistry 278, 123-131.
Buchi et al., "Synthese und pharmakologische wirkung von substituierten Syulfonalen", 1368-1374.
Little et al., "The Intramolecular Michael Reaction"., Organic Reactions, pp. 315-552.

* cited by examiner

*Primary Examiner*—James J. Seidleok
*Assistant Examiner*—Olga Asinovsky
(74) *Attorney, Agent, or Firm*—Kathleen Neuner Manne; Lynne M. Blank

(57) ABSTRACT

An element for the attachment of protein arrays, the element comprising a surface to which are attached a plurality of piperazine functional groups wherein the piperazine functional groups are represented by Formula I:

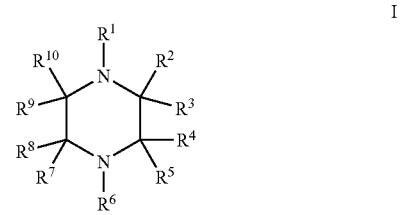

where
$R^1, R^2, R^3, R^4, R^5, R^6, R^7, R^8, R^9, R^{10}$, are hydrogen, alkyl, alkenyl, alkynyl, alkylhalo, cycloalkyl, cycloalkenyl, alkylthio, alkoxy, with the proviso that at least one of $R^1$ to $R^{10}$ be a non-labile chemical unit that attaches the piperazine functional group to the surface of the element.

10 Claims, No Drawings

ELEMENT FOR PROTEIN MICROARRAYS

FIELD OF THE INVENTION

The present invention relates to fabricating protein microarrays in general and in particular to an element that has been modified to multiple and specific attachment of biological molecules.

BACKGROUND OF THE INVENTION

The completion of Human Genome project spurred the rapid growth of a new interdisciplinary field of proteomics which includes: identification and characterization of complete sets of proteins encoded by the genome, the synthesis of proteins, post-translational modifications, as well as detailed mapping of protein interaction at the cellular regulation level.

While 2-dimensional gel electrophoresis in combination with mass spectrometry still remains the dominant technology in proteomics study, the successful implantation and application of DNA microarray technology to gene profiling and gene discovery have prompted scientists to develop protein microarray technology and apply microchip based protein assays to the field of proteomics. For example, in WO 00/04382 and WO 00/04389, a method of fabricating protein microarrays is disclosed. A key element in the disclosure is a substrate consisting of a solid support coated with a monolayer of thin organic film on which protein or a protein capture agent can be immobilized.

Nitrocellulose membrane was widely used as a protein blotting substrate in Western blotting and enzyme linked immunosorbent assay (ELISA). In WO 01/40312 and WO 01/40803, antibodies are spotted onto a nitrocellulose membrane using a gridding robot device. Such spotted antibody microarrays on a nitrocellulose membrane substrate have been shown to be useful in analyzing protein mixture in a large parallel manner.

In WO 98/29736, L. G. Mendoza et al. describe an antibody microarray with antibody immobilized onto a N-hydroxysuccinimidyl ester modified glass substrate. In U.S. Pat. No. 5,981,734 and WO 95/04594, a polyacrylamide based hydrogel substrate technology is described for the fabrication of DNA microarrays. More recently, in *Anal. Biochem.* (2000) 278, 123–131, the same hydrogel technology was further demonstrated as useful as a substrate for the immobilization of proteins in making protein microarrays.

In the above cited examples, the common feature among these different approaches is the requirement of a solid support that allows covalent or non-covalent attachment of a protein or a protein capture agent on the surface of said support. In DNA microarray technology, a variety of surfaces have been prepared for the deposition of pre-synthesized oligos and PCR prepared cDNA probes. For example, in EP 1 106 603 A2 a method of preparing vinylsulfonyl reactive groups on the surface to manufacture DNA chip is disclosed. In the preferred embodiments in EP 1 106 603 A2, silane coupling agents such as γ-aminopropyltrimethoxysilane are affixed to a glass substrate, referred to as a solid carrier, via covalent bonds to the silyloxy functional group. The pendant primary amino groups are then reacted with vinylsulfonyl compounds such as bis(vinylsulfonyl)methane (BVSM) to provide a reactive surface for attachment of DNA molecules. However, a limitation of this approach is that the reactions of primary amines with bis(vinylsulfones) like BVSM can lead to cyclizations via intramolecular Michael additions (reviewed in Little, R. D.; Masjedizadeh, M. R.; Wallquist, O.; McLoughlin, J. I., *Organic Reactions*; New York; Wiley, 1995, pp. 315–552), which result in the loss of both the amino and the vinylsulfonyl group. An example of a cyclization reaction involving a primary amine and a BVSM derivative has also been reported (Buchi, J.; Fueg, H. R.; Aebi, A. *Helv. Chim. Acta* 1959, 42, 1368–1374).

Moreover, even though the invention in EP 1 106 603 A2 may be useful in preparing DNA chip, it is not suitable for protein microarray applications. Unlike DNA, proteins tend to bind to surfaces in a non-specific manner and, in doing so, lose their biological activity. Thus, the attributes for a protein microarray substrate are different from those for a DNA microarray substrate in that the protein microarray substrate must not only provide surface functionality that are capable of interacting with protein capture agents, but must also resist non-specific protein binding to areas where no protein capture agents have been deposited.

Bovine serum albumin (BSA) has been demonstrated to be a useful reagent in blocking proteins from non-specific surface binding. Polyethylene glycol and phospholipids have also been used to passivate surfaces and provide a surface resistant to non-specific binding. However, all of these methods suffer disadvantages either because surface preparation takes a long time or because the method of surface modification is complex and difficult, making the method less than an ideal choice for large scale industrial manufacture.

U.S. Ser. No. 10/020,747 describes a low cost method of making protein microarray substrate using gelatin coating to create a reactive surface for immobilization of protein capture agents. While the gelatin modified surface effectively eliminates non-specific protein binding, the number of reactive sites on the surface are limited by the intrinsic functional groups in gelatin and the type of chemical agents (A-L-B) employed. Since the number of reactive sites on the surface directly determines the ultimate signal detection limit, it is desirable to create a surface with higher number of reactive sites that serves as a matrix on a solid support for the attachment of protein capture agents. The art needs a substrate with chemical functionality for the immobilization of protein capture agents, but such substrate must not bind proteins to areas on the gelatin surface that are without immobilized protein capture agents.

USSN 2003/0170474 A1 describes combinations of polymers, gelatin, and crosslinkers that are claimed to provide improved preparations of protein arrays. The polymers are referred to as scaffolds and are claimed to operate by effectively increasing the density of reactive functional crosslinking groups, such as activated olefins generated on reaction with a crosslinker molecule. These polymers are categorized into two general groups differing in their so-called crosslinking strategies. In one, polymers that contain functional groups that are reactive towards crosslinkers are claimed. Polymers containing groups including phosphines, thiols, and primary and secondary amines, are claimed. These polymers are proposed to increase the density of the desired attached proteins via conversion of these functional groups into groups that are capable of immobilizing proteins. The conversion of the functional groups is claimed to take place via reaction with a bifunctional crosslinking agent. In practice, the combinations of polymers based on the primary amine N-(3-aminopropyl)methacrylamide monomer and poly(ethylene)imine are cited. In addition, polymers containing the nitrogen acid, imidazole, e.g., poly (N-vinylimidazole) are claimed. A second strategy claimed in USSN 2003/0170474 A1 employs polymers which contain functions that are capable of immobilizing proteins, without the addition of a bifunctional agent.

It has since been found that some functional groups, such as nitrogen-containing compounds like amines, exhibit large variations in their reactivities towards certain classes of bifunctional crosslinkers, such as activated olefins like bis (vinylsulfonyl)methane (BVSM). Amines that exhibit low reactivity towards bifunctional crosslinkers are undesirable because they increase the time required to prepare the surface. Moreover, as cited above, certain types of functional groups, such as primary amines, react with crosslinkers like bis(vinylsulfonyl)methane to provide undesirable side products. These side reactions effectively remove both the functional group and the crosslinking agent, decreasing the efficiency of the process and the density of the functional groups. The present invention is designed to provide improvements over the existing art through the use of elements that contain piperazine functional groups that demonstrate improved reactivity towards bifunctional crosslinkers like bis(vinylsulfonyl)methane and are not subject to undesired side reactions such as intramolecular cyclization reactions.

SUMMARY OF THE INVENTION

The invention provides an element for the attachment of protein arrays, the element comprising a surface to which are attached a plurality of piperazine functional groups. The piperazine functional groups are represented by Formula I:

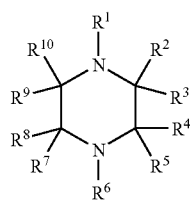

where $R^1$, $R^2$, $R^3$, $R^4$, $R^5$, $R^6$, $R^7$, $R^8$, $R^9$, $R^{10}$ are hydrogen, alkyl, alkenyl, alkynyl, alkylhalo, cycloalkyl, cycloalkenyl, alkylthio, alkoxy, with the proviso that at least one of $R^1$ to $R^{10}$ be a non-labile group which attaches the piperazine to the surface of the element. In the preferred embodiment of the invention, the attachment to the surface is formed via a covalent bond.

Another embodiment of the invention discloses an element for the attachment of protein arrays, the element comprising a surface to which are attached a plurality of piperazine functional groups;

a polymer; and a crosslinking compound A-L-B;

wherein A is a functional group capable of interacting with the piperazine group; L is a linking group capable of interacting with A and with B; and B is a functional group capable of interacting with a protein capture agent.

In the preferred embodiment of the invention, the piperazine functional groups are incorporated into a polymer. In one embodiment, a polymer attached to the surface of the element contains functional groups capable of reacting with piperazine, and the piperazine is attached to the polymer through a subsequent chemical reaction. In a more preferred embodiment, the piperazine groups are part of a piperazine-containing polymer that is attached to the surface of the microarray element.

In a still more preferred embodiment of the invention, the piperazine-containing polymer is attached to a substrate prepared with gelatin.

The element of the invention containing piperazine functional groups is particularly useful because of the high reactivity of the piperazine functional groups towards certain crosslinking compounds (A-L-B) as compared to elements with functional groups of the type known in the art. The use of elements containing piperazine groups of the invention also precludes formation of some undesirable side products formed in the reactions of some amines of the type known in the art with certain crosslinking compounds. The combination of high reactivity and selectivity of the piperazine functional groups leads to rapid and efficient functionalization of substrates for attachment of molecules of interest, such as proteins. The combination of high reactivity and selectivity of the piperazine functional groups of the invention towards certain crosslinkers as compared to other amines and nitrogen-containing compounds is demonstrated below in examples. The usefulness of the claimed element for protein attachment showing improved signal to noise is also demonstrated below in the examples.

DETAILED DESCRIPTION OF THE INVENTION

In general, a protein microarray can be prepared by first modifying a solid substrate, namely the protein microarray substrate, followed by depositing various protein capture agents onto the modified surface at pre-defined locations. As used herein, the term "substrate" refers to a surface modified for subsequent immobilization of protein capture agents. The substrate is coated on a base, referred to as a "support." Supports of choice for protein microarray applications can be organic, inorganic or biological. Some commonly used support materials include glass, plastics, metals, and semiconductors. The support can be transparent or opaque, flexible or rigid. In some cases, the support can be a porous membrane such as nitrocellulose and polyvinylidene difluoride, and the protein capture agents are deposited onto the membrane by physical adsorption. However, to improve robustness and reproducibility, it is more desirable to immobilize the protein capture agents through covalent bonding to the modified support. For dimensional stability, glass is a preferred support material.

In the present invention, it is preferred that the substrate contain an interlayer, i.e., a layer between the support and the surface containing the functional groups useful in the immobilization of proteins. Gelatin is the preferred interlayer material. A definition of gelatin found useful to this invention may be found in US 2003/0170474 A1.

In the case of gelatin as the preferred interlayer material, an organic solvent, or a mixture of solvents, should also be included in the formulation. Examples of such organic solvent include, but are not limited to, acetone, alcohol, ethyl acetate, methylene chloride, ether, or a mixture of the foregoing. In order to uniformly mix gelatin with these organic solvents, a dispersing aid can be, but is not necessarily, added to the formulation, e.g., organic acids or bases. To improve adhesive strength of the interlayer, silicate salt, e.g. sodium silicate, is also included in the interlayer formulation. To improve the physical strength of the interlayer, it is preferred that gelatin in the interlayer is hardened using one or more than one crosslinking agent. Examples of gelatin hardening agents can be found in standard references such as *The Theory of the Photographic Process*, T. H. James, Macmillan Publishing Co., Inc. (New York 1977) or in *Research Disclosure*, September 1996, Number 389, Part IIB (hardeners). Inorganic hardening agents are preferred over organic hardeners.

When polymer support is used, surface treatment is necessary to render the appropriate adhesiveness for binding the interlayer. For example, discharge treatment, flame treatment, ultraviolet ray treatment, high frequency treatment, active plasma treatment, laser treatment, glow discharge, LTV exposure, electron-beam treatment or the like as described in U.S. Pat. Nos. 2,764,520, 3,497,407, 3,145,242, 3,376,208, 3,072,483, 3,475,193, 3,360,448, British Patent No. 788,365, etc., can be used. Polymer supports can be surface-treated with adhesion-promoting agents including dichloroacetic acid and trichloroacetic acid, phenol derivatives such as resorcinol and p-chloro-m-cresol, solvent washing prior to overcoating with a subbing interlayer, e.g. the gelatin interlayer described above. In addition to surface treatment or treatment with adhesion promoting agents, additional adhesion promoting primer or tie layers containing polymers such as vinylidene chloride-containing copolymers, butadiene-based copolymers, glycidyl acrylate or methacrylate-containing copolymers, maleic anhydride-containing copolymers, condensation polymers such as polyesters, polyamides, polyurethanes, polycarbonates, mixtures and blends thereof, and the like may be applied to the polyester support. Particularly preferred primer or tie layers comprise a chlorine containing latex or solvent coatable chlorine containing polymeric layer. Vinyl chloride and vinylidene chloride containing polymers are preferred as primer or subbing layers of the present invention.

For an example of a protein array substrate in one embodiment of this invention, a glass surface is coated with a gelatin interlayer to provide a hydrophilic surface for the subsequent coating of a polymer containing functional groups of the invention. This substrate is treated with a crosslinking agent in order to attach protein capture agents.

In general, to immobilize the protein capture agents onto a solid substrate, it is often necessary to modify the substrate. The substrate is modified via reaction with certain crosslinking compounds which can be represented as A-L-B. Herein, A is a chemical functional group capable of reacting or interacting with the substrate, B is a chemical functional group capable of reacting or interacting with the protein capture agent and L is a linking group. Preferably, L is a diradical of such a length that the shortest through-bond path between the ends that connect A to B is not greater than 10 atoms.

There are two classes of bi-functional agents: 1). homofunctional agent if A=B; and 2). heterofunctional agent if A≠B. Some commonly used A and B include but are not limited to, aldehyde, epoxy, hydrazide, vinylsulfone, succinimidyl ester, carbodiimide, maleimide, dithio, iodoacetyl, isocyanate, isothiocyanate, aziridine. The linking group L comprises any combination of non-labile covalently bonded chemical units sufficient to connect the two functionalities A and B. These chemical units can consists of, but are not necessarily limited to, a single bond, a carbon atom, an oxygen atom, a sulfur atom, a carbonyl group

a carboxylic ester group

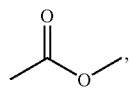

a carboxylic amide group

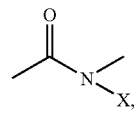

a sulfonyl group

a sulfonamide group

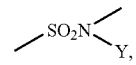

an ethyleneoxy group, a polyethyleneoxy group, or an amino group

where substituents X, Y, and Z are each independently a hydrogen atom, or an alkyl group of 1–10 carbon atoms; and linear or branched, saturated or unsaturated alkyl group of 1 to 10 carbon atoms (such as methyl, ethyl, n-propyl, isopropyl, t-butyl, hexyl, decyl, benzyl, methoxymethyl, hydroxyethyl, iso-butyl, and n-butyl); a substituted or unsubstituted aryl group of 6 to 14 carbon atoms (such as phenyl, naphthyl, anthryl, tolyl, xylyl, 3-methoxyphenyl, 4-chlorophenyl, 4-carbomethoxyphenyl and 4-cyanophenyl); and a substituted or unsubstituted cycloalkyl group of 5 to 14 carbon atoms such as cyclopentyl, cyclohexyl, and cyclooctyl); a substituted or unsubstituted, saturated or unsaturated heterocyclic group (such as pyridyl, pyrimidyl, morpholino, and furanyl); a cyano group. Some solubilizing groups can also be introduced into A-L-B and examples of these solubilizing groups include, but are not limited to, carboxylic acid, sulfonic acid, phosphonic acid, hydroxamic acid, sulfonamide, and hydroxy groups (and their corresponding salts). A and B can also be in the form of readily reactive functionalities towards crosslinkers, examples include but are not limited to carboxy, amino, and chloromethyl, etc. A and B can be affinity tags that are capable of interacting non-covalently with the protein capture agents intended to be immobilized onto the substrate. For example, some commonly used tag systems include, but are not limited to, streptavidin and biotin, histidine tags and nickel metal ions, glutathione-S-transferase and glutathione. One skilled in the art should be able to create a fusion protein capture agent using recombination DNA technology and an element of tag recognition unit can be introduced into protein capture agent in this way.

In the present invention, crosslinking compounds that incorporate vinylsulfonyl groups are preferred. Examples of vinylsulfonyl crosslinking compounds include but are not limited to those compounds disclosed in EP 1 106 603 A2 (incorporated herein by reference). Still more preferred are homofunctional crosslinking compounds A-L-B containing vinylsulfonyl groups. Examples of homofunctional crosslinkers A-L-B include but are not necessarily limited to bis(vinylsulfonyl)methane (BVSM), bis(vinylsulfonylmethyl)ether (BVSME), and bis(vinylsulfonylacetamido)ethane (BVSAE). Most preferred is bis(vinylsulfonyl)methane (BVSM).

The present invention is designed to overcome some of the deficiencies of the existing art in protein immobilization. Specifically the art needs functional groups that are useful in the immobilization of proteins, but that do not suffer from problems associated with low reactivity towards crosslinking compounds, such as long reaction times, and are not subject to undesirable side reactions with crosslinking compounds that result in loss of the ability to immobilize proteins. The combination of higher reactivity towards crosslinkers and prevention of side reactions is attained through the use of functional groups designed to address both issues. The functional groups found to be useful to this invention are piperazines.

The piperazine functional groups have the formula I.

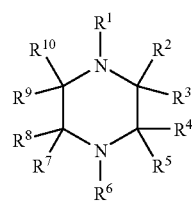

Where $R^1$, $R^2$, $R^3$, $R^4$, $R^5$, $R^6$, $R^7$, $R^8$, $R^9$, $R^{10}$, are hydrogen, alkyl, alkenyl, alkynyl, alkylhalo, cycloalkyl, cycloalkenyl, alkylthio, alkoxy, with the proviso that at least one of the groups be a linkage group. The linkage group L' comprises any combination of non-labile covalently bonded chemical units sufficient to connect the piperazine functional group to the substrate. Examples of linkage groups include covalent bonds. One example of a linkage group includes, but is not limited to, crosslinking compounds (A-L-B, as defined above). Further examples of linkage groups L' include, but are not limited to the previously cited examples of chemical units specified for A (or B) in the specifications for A-L-B. In a preferred embodiment of the invention the linkage groups L' are attached to a polymer. In one embodiment of the invention the piperazine functional groups are incorporated into the polymer in situ, i.e., the piperazine groups are incorporated into the polymer after the polymer has been attached to the substrate. This can be done by one skilled in the art through reaction of piperazines with a polymer that contains groups that are capable of reacting with piperazine. For example, the polymer may contain reactive moieties that are capable of being displaced by piperazine such as halo groups, like chloro, bromo, and iodo groups, or the polymer may contain groups that are subject to addition reactions in the presence of piperazine, such as Michael acceptors (a review of some representative Michael acceptors may be found in Bernasconi, C. F. *Tetrahedron* 1989, 13, 4017–4090). These examples of in situ reactions are meant to be illustrative rather than limiting. In a preferred embodiment of the invention, the piperazine is incorporated into the polymer before the polymer is attached to the substrate. The polymer may incorporate piperazine as part of the polymer backbone or through attachment to the polymer backbone (Scheme 1).

Scheme 1. Piperazine Containing Polymers.

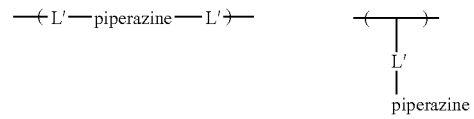

Although the piperazine containing polymer may have any molecular weight, number average molecular weights (Mn) between 1000 and 200,000 AMU are preferred. Molecular weights (Mn) between 2000 and 50,000 AMU are especially preferred.

In an even more preferred embodiment of the invention, at least one of the substituents $R^1$ and $R^6$ in Formula I is hydrogen. Still more preferred are piperazine containing polymers of the type shown in Formula I where one of the substituents chosen between $R^1$ and $R^6$ in Formula I is hydrogen, and one of the substituents chosen between $R^1$ and $R^6$ is a linking group (L') (Formula Ia).

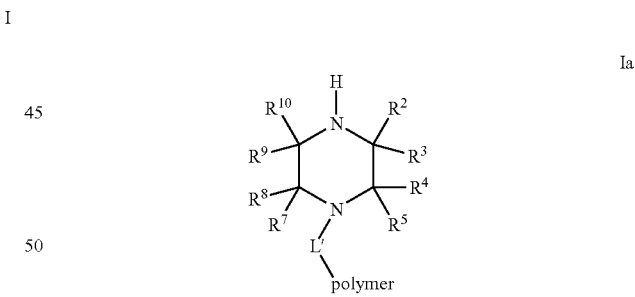

Even more preferred are piperazine containing polymers as in Formula Ia in which the substituents $R^1$, $R^2$, $R^3$, $R^4$, $R^5$, $R^7$, $R^8$, $R^9$, $R^{10}$, are hydrogen.

The compounds of the invention are basic in nature. As such, they react with any of a number of inorganic and organic acids to form addition salts. Included within the scope of the invention are mono- and di-salts. Commonly used inorganic acids used to form such salts include but are not necessarily limited to hydrochloric acid, hydrobromic acid, hydroiodic acid, sulfuric acid, and phosphoric acid, and commonly used organic acids include but are not necessarily limited to p-toluenesulfonic acid, methanesulfonic acid, oxalic acid, carbonic acid, succinic acid, citric acid, benzoic acid, and acetic acid.

Many of the compounds in formula I are isomers. This invention is not limited to any particular isomer but includes all possible individual isomers and racemates.

Once a solid support, the corresponding interlayer formulation, and the surface layer formulation are selected, it is preferred that the interlayer and the surface layer containing the piperazine functional groups may be applied to the solid support using an in-line process during the microarray substrate manufacture. However, it may also be made in separate processes. The interlayer and the surface layer can be coated on the support using the methods that are broadly described by Edward Cohen and Edgar B. Gutoff in Chapter 1 of "Modern Coating And Drying Technology", (Interfacial Engineering Series; v.1), (1992), VCH Publishers Inc., New York, N.Y. To achieve ultra thin film coating with the interlayer application, it is desirable that the interlayer is coated using either gravure method, as described in U.S. Pat. Nos. 3,283,712, 3,468,700, and 4,325,995, or wicked coating method, as described in U.S. Pat. Nos. 3,000,349, 3,786,736, 3,831,553, and 4,033,290.

Once a protein microarray substrate is modified with the piperazine functional groups, protein capture agents will be placed onto the substrate to generate protein microarray content. A protein molecule consists of 20 amino acids that are connected in linear manner covalently. Some proteins can be further modified at selected amino acids through posttranslational processes that include phosphorylation and glycosylation. A protein molecule can be used as a protein capture agent. As used herein, the term "protein capture agent" means a molecule that can interact with proteins in high affinity and high specificity. Typically it is desirable to have an affinity binding constant between a protein capture agent and target protein greater than $10^6$ $M^{-1}$. There are several classes of molecules that can be used as protein capture agents on a protein microarray. Antibodies are a class of naturally occurring protein molecules that are capable of binding targets with high affinity and specificity. The properties and protocols of using antibodies can be found in "*Using Antibodies; A Laboratory Manual*", (Cold Spring Harbor Laboratory Press, by Ed Harlow and David Lane, Cold Spring Harbor, N.Y. 1999). Antigens can also be used as protein capture agents if antibodies are intended targets for detection. Examples include phosphotases, kinases, proteases, oxidases, hydrolases, cytokines, or synthetic peptides. Nucleic acid ligands can be used as protein capture agent molecules after in vitro selection and enrichment for their binding affinity and specificity to certain targets. The principle of such selection process can be found in *Science*, Vol. 249, 505–510, 1990 and *Nature*, Vol. 346, 818–822, 1990. U.S. Pat. No. 5,110,833 discloses an alternative class of synthetic molecules that can mimic antibody binding affinity and specificity and can be readily prepared by the so-called Molecular Imprinting Polymer (MIP). This technology has been reviewed in *Chem. Rev.* Vol. 100, 2495–2504, (2000).

In practice, a protein microarray is brought into contact with a biological fluid sample, proteins in the sample will adsorb to both areas spotted with specific protein capture agents and areas without protein capture agents. Since the protein microarray is intended to be used for the measurement of specific interactions between protein capture agents on the chip with certain proteins or other molecules in the biological fluid sample, the non-specific binding of sample proteins to non-spotted area would give rise to high background noise. The term non-specific binding refers to the tendency of protein molecules to adhere to a solid surface in a non-selective manner. This high background noise resulting from the non-specific binding will interfere with reporter signals to be detected from the spotted area unless the non-specific binding is blocked in an appropriate manner. Typically, the protein microarray will be immersed in a solution containing a blocking agent to block the non-specific binding sites before its contact with the intended analyte solution. A commonly used method for blocking protein non-specific binding is to treat the surface of the substrate with a large excess of bovine serum albumin. The non-spotted surface area may also be chemically modified with polyethylene glycol (PEG), phospholipid, or polylysine to prevent non-specific binding.

The reactivities of the invention compounds as well as those of the types of compounds known in the art have been determined by the corresponding relative rate constants for the reactions of the relevant functional groups with a representative bifunctional activated olefin crosslinking agent, bis(vinylsulfonyl)methane (BVSM), in neutral aqueous solution. Compounds of the invention are also compared to examples of compounds known in the art with regard to undesired cyclization reactions. In this invention, a new class of polymeric material based on piperazines has also been invented for enhancing protein immobilization. In a preferred embodiment, a piperazine containing polymer has been used and it shows unexpected reactivity enhancement versus primary amine and secondary amine containing polymers as well as imidazole containing polymers of the type known in the art. Moreover, when a piperazine containing polymer is incorporated into a protein microarray substrate, the material has been demonstrated to attain higher densities of protein immobilization than a comparison protein microarray element.

The invention can be better appreciated by reference to the following specific embodiments.

EXAMPLE 1

This example illustrates the reactivity advantage towards vinylsulfones of compounds of the invention over amines and imidazoles of the type known in the art.

Reactivity data for compounds of the invention as well as comparison compounds are thus gathered in Table 1. The reactivities of the molecules were determined based on their relative rate constants for reaction with bis(vinylsulfonyl) methane (BVSM). The relative rate constants were determined from kinetic experiments. General procedures for the design and interpretation of kinetic experiments may be found in Espenson, J. H. *Chemical Kinetics and Reaction Mechanisms*; McGraw-Hill: New York, 1981.

Scheme 2. Comparison Model Compounds and Comparison Monomers.

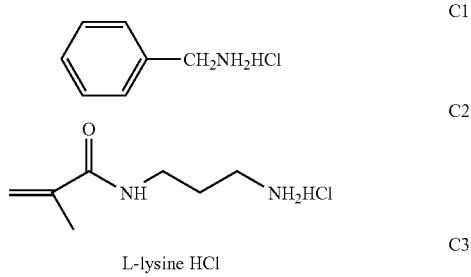

-continued

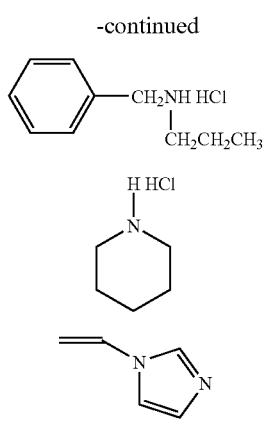

Scheme 3. Invention Monomers.

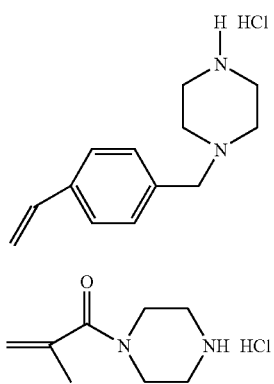

TABLE 1

Reactivity of Nucleophiles towards BVSM.

| cmpd[a] | type | $k_{rel}$[b] |
|---|---|---|
| C1 | comp. | 0.03 |
| C2 | comp. | 0.01 |
| C3 | comp. | 0.02 |
| C4 | comp. | 0.03 |
| C5 | comp. | 0.02 |
| C6 | comp. | 0.02 |
| I1 | inv. | 1 |
| I2 | inv. | 1 |

[a]See Schemes 2 and 3 for relevant compounds.
[b]Relative bimolecular rate constant for reaction with bis(vinylsulfonyl) methane (BVSM).

From the data in Table 1, it is evident that monomers that contain piperazine groups are significantly more reactive (30× to 100× more reactive based on relative rate constants) than model compounds (C1) or monomers (C2, C3) that contain primary amines of the type known in the art. Moreover, the data in Table 1 show that piperazine monomers (1-(4-vinylbenzyl)piperazine hydrochloride (I1), and methacrylic acid piperazine amide hydrochloride (I2)) are significantly more reactive than model secondary amines (C4, C5) of the type known in the art. It is noteworthy that piperidine, the simple cyclic analog of piperazine, is 50× less reactive towards vinylsulfones than the monomers of the invention (I1,I2). In addition to the relatively high reactivity displayed by compounds of the invention relative to amines of the type known in the art, the compounds of the invention (I1,I2) are found to exhibit markedly higher reactivity (50×) than a nitrogen acid (N-vinylimidazole) of the type known in the art.

EXAMPLE 2

This example illustrates the advantage of compounds of the invention relative to examples from the art, regarding undesired side reactions. In this case, the formation of undesired cyclic adducts due to intramolecular Michael addition reactions is considered. Primary amines of the type previously disclosed can react with crosslinkers such as BVSM to give cyclic adducts (Scheme 4). By contrast compounds of the invention are not observed to undergo cyclization reactions (Table 2).

Scheme 4. Cyclization Reaction of BVSM with Primary Amines.

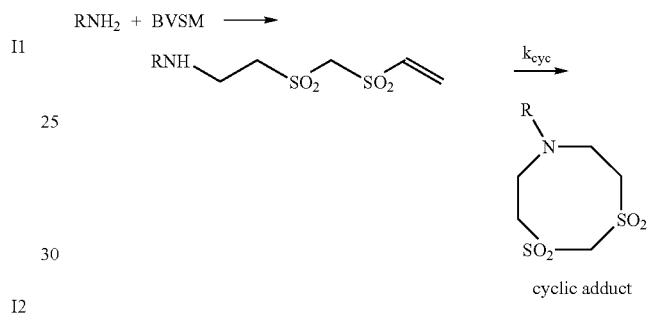

cyclic adduct

TABLE 2

Cyclization Reactions of BVSM with Nucleophiles.

| cmpd | type | $k_{cyc}$ (min$^{-1}$) | yield[a] |
|---|---|---|---|
| C1 | comp. | 1.8 | 63% |
| I1 | inv. | n.o.[b] | n.o. |
| I2 | inv. | n.o. | n.o. |

[a]Isolated yield of cyclic adduct from reaction of BVSM (0.6 mmol) with C1 (2.67 mmol) in 100 mL of phosphate buffer (pH 6, 0.3 μ (ionic strength)).
[b]n.o. = no cyclization observed.

EXAMPLE 3

Preparation of Invention Polymer I3

A three-liter, three-necked round-bottomed flask fitted with a mechanical stirrer, reflux condenser, and nitrogen inlet was charged with 180 g of tetrahydrofuran, 160 g of distilled water, 2.84 g of acrylamide, 14.29 g of 1-(4-vinylbenzyl)piperazine dihydrochloride, and 42.99 g of a 53.2 wt % solution of 2-acrylamido-1-methylpropane-1-sulfonic acid, sodium salt. This solution was sparged with nitrogen for 30 min, and then 0.20 g of 2,2'-azobisisobutyronitrile was added. The reaction mixture was stirred under nitrogen at 60° C. overnight. The viscous reaction mixture was removed from the flask and dialyzed with Membra-Cel® dialysis tubing (12,000–14,000 molecular weight cut-off) for 5 hr against deionized distilled water.

This example illustrates the reactivity advantage towards vinylsulfones of compounds of the invention over amines and imidazoles of the type known in the art in polymeric states.

The data in Table 3 show that when monomers of the invention are incorporated into a polymer, the piperazine retains its high relative reactivity. In fact, the piperazine-containing polymer I3 is found to be the most reactive towards the vinylsulfone BVSM, as compared to a range of polymers of the type known in the art, including primary amine containing polymers (C7, C8), secondary amine containing polymers (C9), and polymers containing nitrogen acids (imidazolyl groups) of the type known in the art (C10, C11).

Scheme 5. Comparison Polymers poly(N-(3-aminopropyl)methacrylamide) HCl    C7 poly-L-lysine HBr    C8 polyethylenimine    C9 poly(n-vinylimidazole)    C10

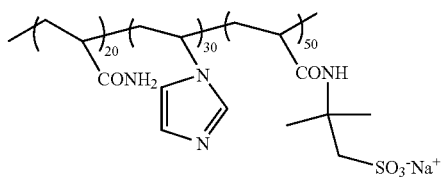

C11

Scheme 6. Invention Polymer

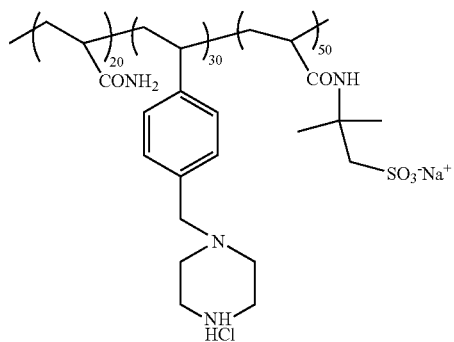

TABLE 3

Polymer Reactivities.

| polymer[a] | type | $k_{rel}$[b] |
|---|---|---|
| C7 | comp. | 0.01 |
| C8 | comp. | 0.06 |
| C9 | comp. | 0.08 |
| C10 | comp. | 0.09 |
| C11 | comp. | 0.10 |
| I3 | inv. | 1.0 |

[a]See Schemes 5, 6 for relevant polymers.
[b]Relative bimolecular rate constant for reaction with bis(vinylsulfonyl)methane (BVSM).

EXAMPLE 4

This example illustrates the modification of coated gelatin surface using a polymeric secondary amine to enhance its protein immobilizaton capacity.

Formulation 1-1 (interlayer melt):

This was prepared by adding 2.5 grams of gelatin, 16.3 grams of chrom-alum, 34.7 grams of methanol, 12.7 grams of sodium silicate in 33.9 grams of distilled water.

Formulation 1-2 (polymer melt 1, invention):

This was prepared by adding 440 grams of bis(vinylsulfonyl)methane solution (1.8% w/w) and 45 grams of invention polymer solution (I3, 16.8% in water), 6.7 grams of coating aid nonylphenoxypolyglycerol, 7.4 grams of coating aid Sodium octyl phenol poly (etheneoxy)sulfonate.

Formulation 1-3 (polymer melt 2, comparison):

Solution 1: This was prepared by adding 726.54 grams of swollen Type IV gelatin (24.8% w/v) in 2237.06 grams of water, 16 grams of coating aid of Nonylphenoxypolyglycerol, 20.4 grams of coating aid Sodium octyl phenol poly (ethenoxy)sulfonate.

Solution 2: This was prepared by adding 800.79 grams of bis(vinylsulfonyl)methane solution (1.8% w/v) and 2199 grams of distilled water.

Solution 1 and solution 2 were mixed in equal volumes in order to make a single melt before coating.

Formulation 1-1 was coated by a Gravure method onto a glass surface to give a so-called "subbed" glass plate. The invention melt (Formulation 1-2) and the comparison melt (Formulation 1-3) were each then introduced onto such subbed glass plates through a wicker coater. The coatings were chill-set in a 9.1 meter long chilling section that was maintained at a temperature of 4° C. and 56.6% RH and then dried in 3 drying sections that totaled 34 meters at a temperature and RH of 35° C. and 18.3% RH respectively.

EXAMPLE 5

This example illustrates the method of evaluating coated protein microarray substrate using a modified enzyme linked immunosorbent assay (ELISA).

The procedure to perform the modified ELISA is follows.
1. Goat anti-mouse antibody IgG from Sigma was dissolved in PBS (phosphate saline buffer, pH 7.4) buffer to a concentration of 1 mg/mL. A series of diluted goat anti-mouse antibody IgG were spotted onto the coated substrates. The spotted substrates were incubated in a humid chamber for 1 hour at room temperature.
2. The substrates were washed four times in PBS buffer with 1% Triton X100™, 5 min each time with shaking.
3. The washed substrates were incubated in PBS buffer with 1% glycine for 15 min with constant shaking.
4. The substrates were washed four times in PBS buffer with 1% Triton™ X100 with shaking.
5. Mouse IgG from Sigma was diluted in PBS buffer with 0.1% Tween™ 20 to 1 μg/mL to cover the whole surface of the substrates, and the substrates were incubated at room temperature for 1 hour.
6. The substrates were washed four times with PBS buffer with 1% Triton X100, 5 min each time with constant shaking.
7. The substrates were incubated in goat anti-mouse IgG horse raddish peroxidase conjugate (diluted in PBS with 1% glycine to appropriate titer) solution to cover the whole surface of the substrates at room temperature for 1 hour with shaking.

8. The substrates were washed four times with PBS buffer with 1% Triton X100, 5 min each time with constant shaking, and rinsed twice in water.

9. The color was developed in horse raddish peroxidase substrate solution containing SuperSignal® ELISA chemiluminescence substrate solution (purchased from PIERCE ENDOGEN). The chemiluminescence image was captured by contacting a thin layer of SuperSignal® ELISA chemiluminescence substrate solution (purchased from PIERCE ENDOGEN) with coated substrate. The emission was measured on Kodak Image Station 440 and quantified using Region of Interest (ROI) software supplied with the instrument.

The signal responses from ELISA assay are summarized in Table 4. Much higher signals were observed for the inventive example versus comparative example from all three antibody concentrations.

TABLE 4

Signal Responses from ELISA Assay

|  | Antibody 1 ng | Antibody 0.2 ng | Antibody 0.1 ng |
| --- | --- | --- | --- |
| Comparison | 13472.44 | 1130 | 597.8889 |
| Invention | 39740.5 | 5184.056 | 2002.667 |

The invention has been described in detail with particular reference to certain preferred embodiments thereof, but it will be understood that variations and modifications can be effected within the spirit and scope of the invention.

What is claimed is:

1. An element for the attachment of protein arrays, the element comprising a surface to which are attached
   a plurality of piperazine functional groups;
   a polymer;
   a crosslinking compound A-L-B;
   wherein A is a functional group capable of interacting with a piperazine functional group of the invention; L is a linking group capable of interacting with A and with B; and B is a specific functionality that provides one or more reactive units capable of interacting with a protein capture agent, and wherein the piperazine functional groups are represented by Formula I:

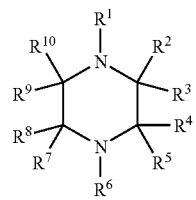

I where
R$^1$, R$^2$, R$^3$, R$^4$, R$^5$, R$^6$, R$^7$, R$^8$, R$^9$, R$^{10}$, are hydrogen, alkyl, alkenyl, alkynyl, alkylhalo, cycloalkyl, cycloalkenyl, alkylthio, alkoxy, with the proviso that at least one of the groups R$^1$ to R$^{10}$ be a linkage group (L').

2. The element in claim 1 wherein at least one of the functional groups A or B in A-L-B is aldehyde, epoxy, hydrazide, vinylsulfone, succinimidyl ester, carbodiimide, maleimide, dithio, iodoacetyl, isocyanate, isothiocyanate, or aziridine.

3. The element in claim 2 wherein at least one of the functional groups in A-L-B is vinylsulfone.

4. The element of claim 1 wherein the linkage group L' comprises any combination of non-labile covalently bonded chemical units sufficient to connect the piperazine functional group to the surface.

5. The element of claim 4 wherein the surface contains a polymer.

6. The element of claim 1 wherein the crosslinking compound A-L-B is bis(vinylsulfonyl)methane, bis(vinylsulfonyl)methyl ether, or bis(vinylsulfonylacetamido) ethane.

7. The element in claim 1 where the crosslinking compound A-L-B is bis(vinylsulfonyl)methane and the piperazine containing polymer comprising 1-(4-vinylbenzyl)piperazine or methacrylic acid piperazine amide monomers, or the corresponding inorganic acid or organic acid addition salts thereof.

8. The element of claim 1 wherein the crosslinking compound A-L-B is bis(vinylsulfonyl)methane and the piperazine polymer is defined by Formula II.

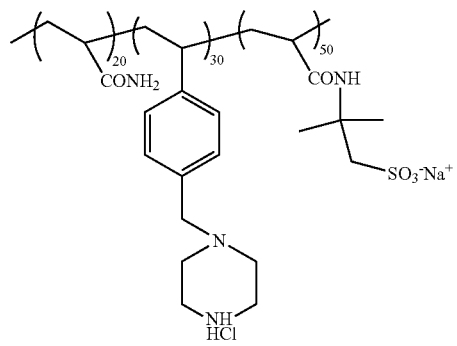

II where 20, 30, and 50 represent the relative molar amounts of each monomeric unit.

9. The element of claim 7 wherein the surface contains gelatin.

10. The element of claim 8 wherein the surface contains gelatin.

* * * * *